(12) United States Patent
Liu (10) Patent No.: US 11,248,761 B1
(45) Date of Patent: Feb. 15, 2022

(54) SMALL NIGHT LAMP WITH SPREADING FRAGRANCE FUNCTION

(71) Applicant: Dongguan Minghuayuan Craft Products Co., Ltd, Dongguan (CN)

(72) Inventor: Shibo Liu, Guang'an (CN)

( * ) Notice: Subject to any disclaimer, the term of this patent is extended or adjusted under 35 U.S.C. 154(b) by 0 days.

(21) Appl. No.: 17/143,161

(22) Filed: Jan. 7, 2021

(30) Foreign Application Priority Data

Nov. 30, 2020 (CN) .......................... 202022840135.2

(51) Int. Cl.
*F21S 8/00* (2006.01)
*F21V 23/04* (2006.01)
*A61L 9/12* (2006.01)
*F21Y 115/10* (2016.01)

(52) U.S. Cl.
CPC ............... *F21S 8/035* (2013.01); *A61L 9/122* (2013.01); *F21V 23/0464* (2013.01); *F21V 23/0471* (2013.01); *A61L 2209/12* (2013.01); *F21Y 2115/10* (2016.08)

(58) Field of Classification Search
CPC ...... F21S 8/035; A61L 9/122; A61L 2209/12; A61L 9/14; A61L 2209/15; A61L 2209/135; A61L 2209/133; F21V 23/0464; F21V 23/0471; F21V 33/00; F21V 33/0024; F21Y 2115/10
See application file for complete search history.

(56) References Cited

U.S. PATENT DOCUMENTS

| | | | | |
|---|---|---|---|---|
| 4,816,973 | A * | 3/1989 | Atalla | F21S 8/035 362/101 |
| 10,413,630 | B1 | 9/2019 | Hsiao | |
| 2007/0122306 | A1* | 5/2007 | Brown | A61L 9/122 422/5 |
| 2007/0207066 | A1* | 9/2007 | Thur | A61L 9/205 422/121 |
| 2011/0027124 | A1 | 2/2011 | Albee et al. | |
| 2013/0265743 | A1* | 10/2013 | Lee | A61L 9/044 362/96 |
| 2016/0195257 | A1* | 7/2016 | Hsiao | F21S 8/035 362/92 |
| 2020/0114038 | A1 | 4/2020 | Yuan | |

* cited by examiner

Primary Examiner — Bao Q Truong (57) ABSTRACT

A small night lamp with spreading fragrance function includes a bottom shell, a fan, a transparent supporting base, a light source and a transparent encloser. The bottom shell is provided with an accommodating groove, the accommodating groove is provided with a first bottom wall and a groove opening, the first bottom wall is provided with a number of air inlet holes. The fan is arranged above the accommodating groove. The inner wall surface of the transparent supporting base is provided with a perforated board, the top surface of the perforated board is provided with a groove for an essential oil piece. The light source is arranged in the transparent supporting base.

20 Claims, 8 Drawing Sheets

SMALL NIGHT LAMP WITH SPREADING FRAGRANCE FUNCTION

TECHNICAL FIELD

The present invention relates to fragrance diffuser technical field, and more particularly, to small night lamp with spreading fragrance function.

BACKGROUND

The Chinese utility model patent CN20192231257.7 discloses a fragrance diffuser, including a base, an essential oil bottle, a cotton stick, an upper cover, a fan and a circuit board. The essential oil bottle is arranged in the base, and the cotton stick is inserted into the essential oil bottle and extends outward the opening of the bottle, the upper cover is covered on the top of the base and is provided with a plurality of holes for diffusing aroma, the fan is electrically connected with the circuit board, the essential oil bottle is installed with a middle fixing base, where the fan is fixedly installed on the middle fixing base and above the cotton stick. The middle fixing base is in shape of a revolving body and is fixed on the outer wall of the opening of the essential oil bottle by threaded connection. The center of the middle fixing base is provided with a central hole corresponding to the opening of the essential oil bottle. The fan is arranged directly above the central hole, and the circuit board is arranged on the middle fixing base.

The above-mentioned fragrance diffuser uses the essential oil bottle to supply essential oil, the essential oil bottle needs to be installed on the middle fixing base by threaded connection, the installation or the replacement is complicated. Moreover, this type of fragrance diffuser only has the function of spreading aroma, its use is relatively simple.

SUMMARY

The object of the invention is to provide a small night lamp with spreading fragrance function, which aims to solve the technical problem that the fragrance diffuser in the prior art uses essential oil bottle to supply essential oil, the essential oil bottle needs to be installed on the middle fixing base by threaded connection, and the installation or the replacement is complicated.

In order to achieve the aforementioned object, the present invention provides

One or more of the technical schemes of the small night lamp with spreading fragrance function provided in the embodiments of the invention have at least one of the following technical effects: the small night lamp with spreading fragrance function is provided with the groove for containing the essential oil piece, the essential oil piece emits fragrance, when the essential oil piece is replaced, it is only need to remove the transparent encloser, then take out the essential oil piece from the groove, and put in a new essential oil piece, which has the advantages of convenient replacement; in addition, the small night lamp with spreading fragrance function also has the function of night lamp besides spreading fragrance, it is practical and variously uses.

BRIEF DESCRIPTION OF THE DRAWINGS

In order to better illustrate the technical scheme in the embodiment of the invention, the following will give a brief description of the drawings to be used in the embodiments or the prior art. It is obvious that the drawings in the following description are only some embodiments of the invention, and for the general technical personnel of the field, other drawings can be obtained on the basis of the drawings without creative effort.

DETAILED DESCRIPTION OF EMBODIMENTS

The embodiments in the present invention are described in detail below, and examples of the embodiments are shown in the drawings where the same or similar labels from beginning to end represent the same or similar elements or elements with the same or similar functions. The embodiments described below by reference to the drawings are exemplary and designed to explain the embodiments of the invention and cannot be understood as limitations on the invention.

As shown in FIG. 1 to FIG. 8, the present invention provides a small night lamp with spreading fragrance function, which includes a bottom shell 100, a fan 200, a transparent supporting base 300, a light source 400 and a transparent encloser 500. The bottom shell 100 is provided with an accommodating groove 110, the accommodating groove 110 is provided with a first bottom wall 111 and a groove opening 112, the first bottom wall 111 is provided with a number of air inlet holes 1111. The bottom shell 100 is also provided with an electrical connector, the accommodating groove 110 is provided with a switch controller. The switch controller is electrically connected with the electrical connector. The fan 200 is arranged above the accommodating groove 110. The transparent supporting base 300 is a first hollow cylinder with a lower opening 310 and an upper opening 320, the lower opening 310 is closely matched with the groove opening 112. In this embodiment, the transparent supporting base 300 is preferably made of acrylic material. In some embodiments, the transparent supporting base 300 can also be made of transparent plastic material or glass material.

Figure 2:
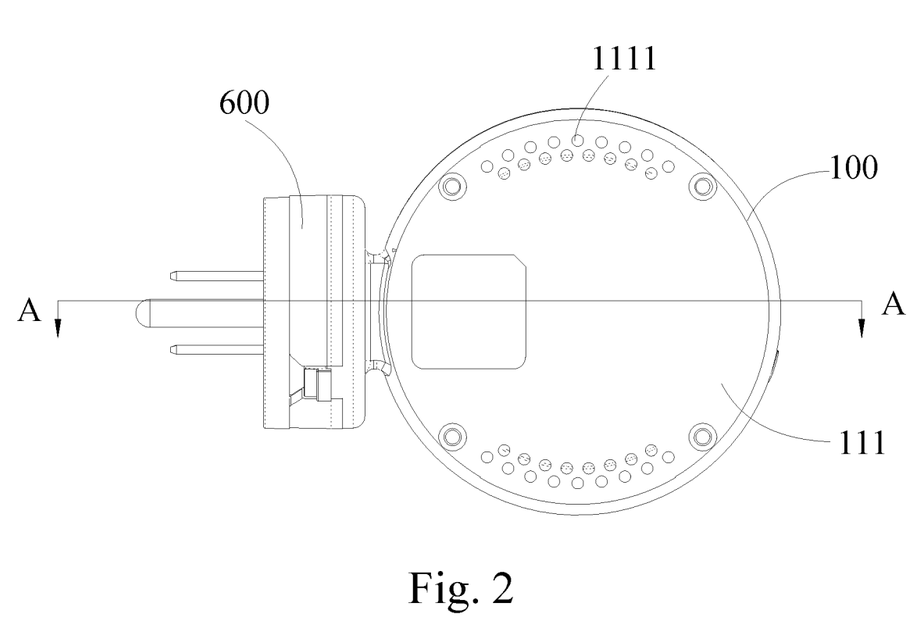
FIG. 2 shows a bottom view of the small night lamp with spreading fragrance function according to the present invention.
Figure 3:
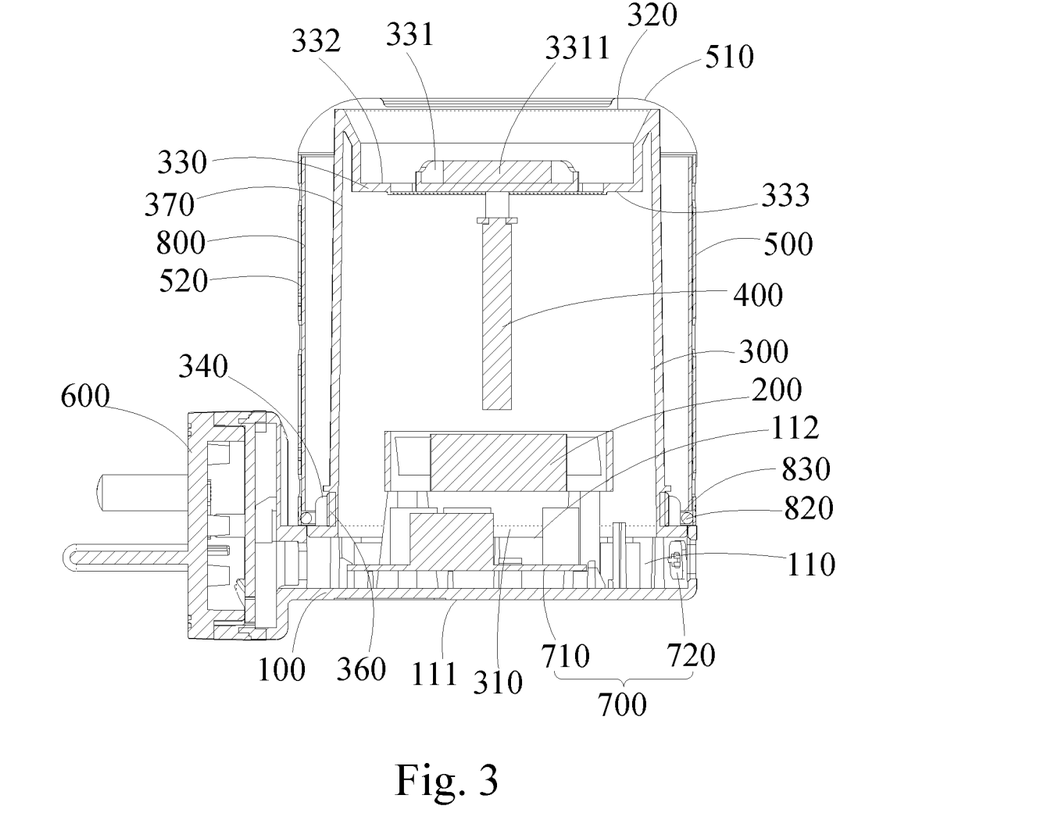
FIG. 3 is a sectional view along the A-A line in FIG. 2.
Figure 4:
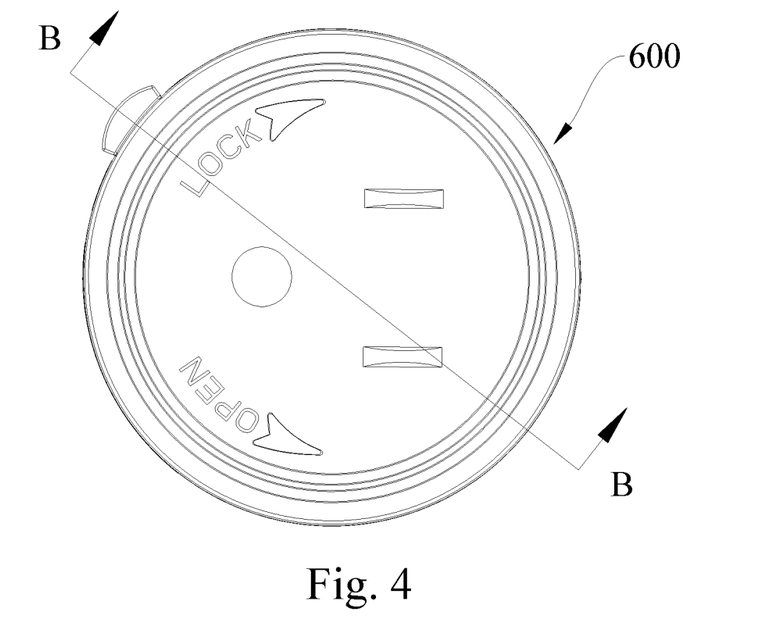
FIG. 4 shows a top view of the replaceable plug according to the present invention.

Referring to FIG. 2 to FIG. 3, a first inner surface 370 of the transparent supporting base 300 is provided with a perforated board 330, a top surface 332 of the perforated board 330 is provided with a groove 331 for an essential oil piece 3311, the essential oil piece 3311 is placed in the groove 331. The light source 400 is arranged in the transparent supporting base 300. The transparent encloser 500 is movably covered an outer side of the transparent supporting base 300, and a bottom edge 350 of the first hollow cylinder is tightly matched with the bottom shell 100. Light emitted by the light source 400 penetrates through the side of the transparent encloser 500. In this embodiment, the transparent encloser 500 is made of porous hollow metal material. In some embodiments, the transparent encloser 500 can also be made of plastic material, glass material or crystal material. A top cover 510 is arranged on the transparent encloser 500, the top cover 510 is correspondingly above the perforated board 330 and a surface of the top cover 510 is provided with a number of air outlet holes 511. The upper opening 320 of the transparent supporting base 300 is closely touch to the top cover 510.

When the small night lamp with spreading fragrance function works, the electrical connector supplies power to the fan 200, the fan 200 pumps the outside air from the air inlet hole into the transparent supporting base 300, the high-speed airflow passes through the perforated board 330 and mixes with the aroma compound evaporated from essential oil piece, and then ejects from the air outlet holes 511 to realize the fragrance expansion. The electrical connector supplies power to the light source 400, and the light source 400 emits light to realize the night light function.

The small night lamp with spreading fragrance function is provided with the groove 331 for containing the essential oil piece 3311, the essential oil piece 331 emits fragrance, when the essential oil piece 3311 is replaced, it is only need to remove the transparent encloser 500, then take out the essential oil piece 3311 from the groove 331, and put a new essential oil piece 3311 in the groove 331, which has the advantages of convenient replacement; in addition, the small night lamp with spreading fragrance function has the function of night lamp besides spreading fragrance, which has practical functions and various uses.

Referring to FIG. 3, in another embodiment of the invention the electrical connector of the small night lamp with spreading fragrance function is a replaceable plug 600. Because of the variety of existing sockets, the replaceable plug 600 is able to adapt to more sockets, which improves the adaptability.

In another embodiment of the invention, the electrical connector of the small night lamp with spreading fragrance function is a fixed plug (not shown).

In another embodiment of the invention, the electrical connector of the small night lamp with spreading fragrance function is USB port (not shown).

Figure 5:
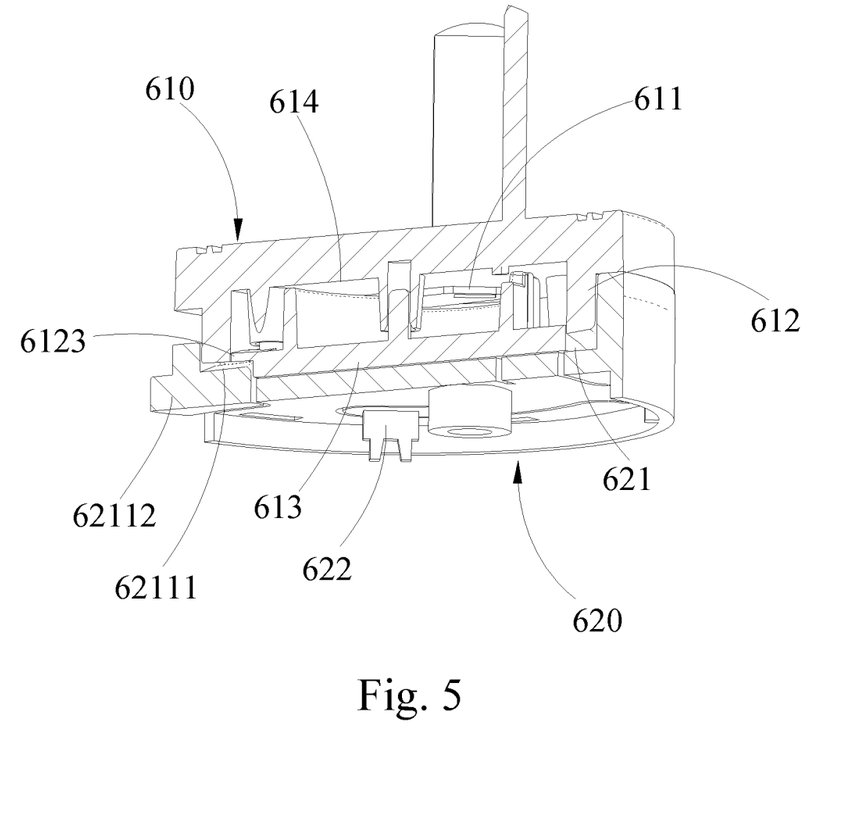
FIG. 5 is a sectional view along the B-B line in FIG. 4.
Figure 6:
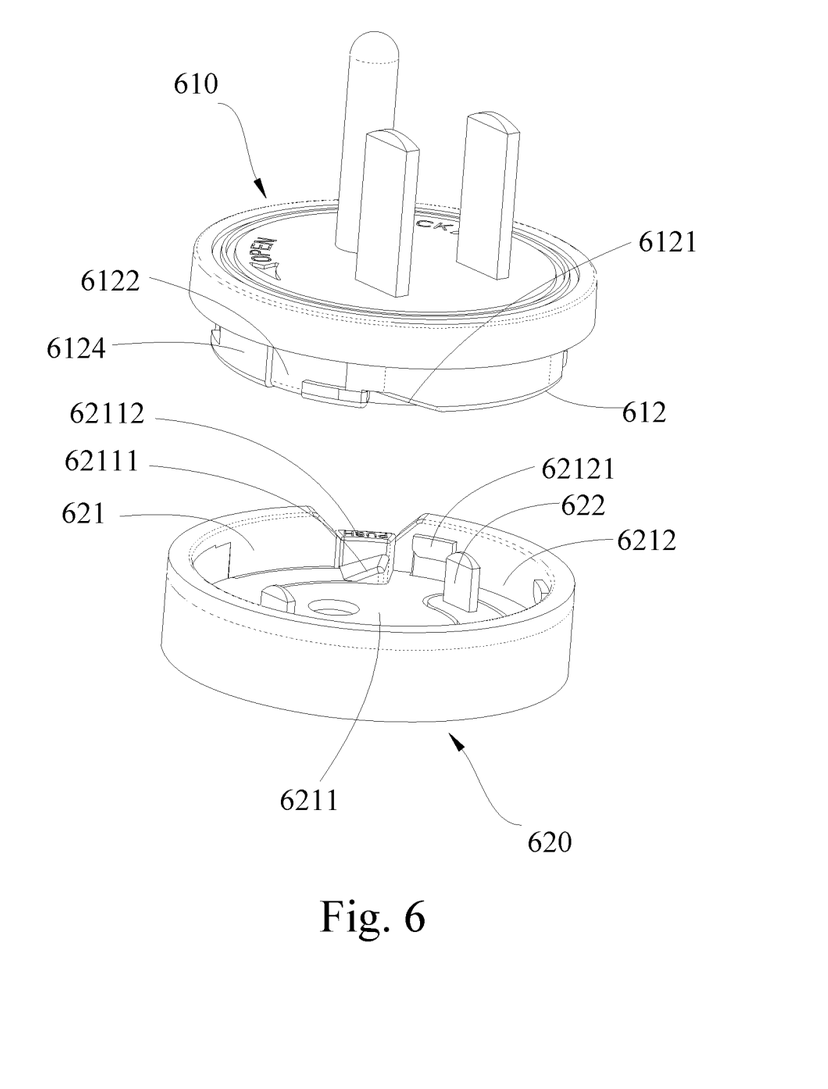
FIG. 6 shows an explosive view of the replaceable plug according to the present invention.
Figure 7:
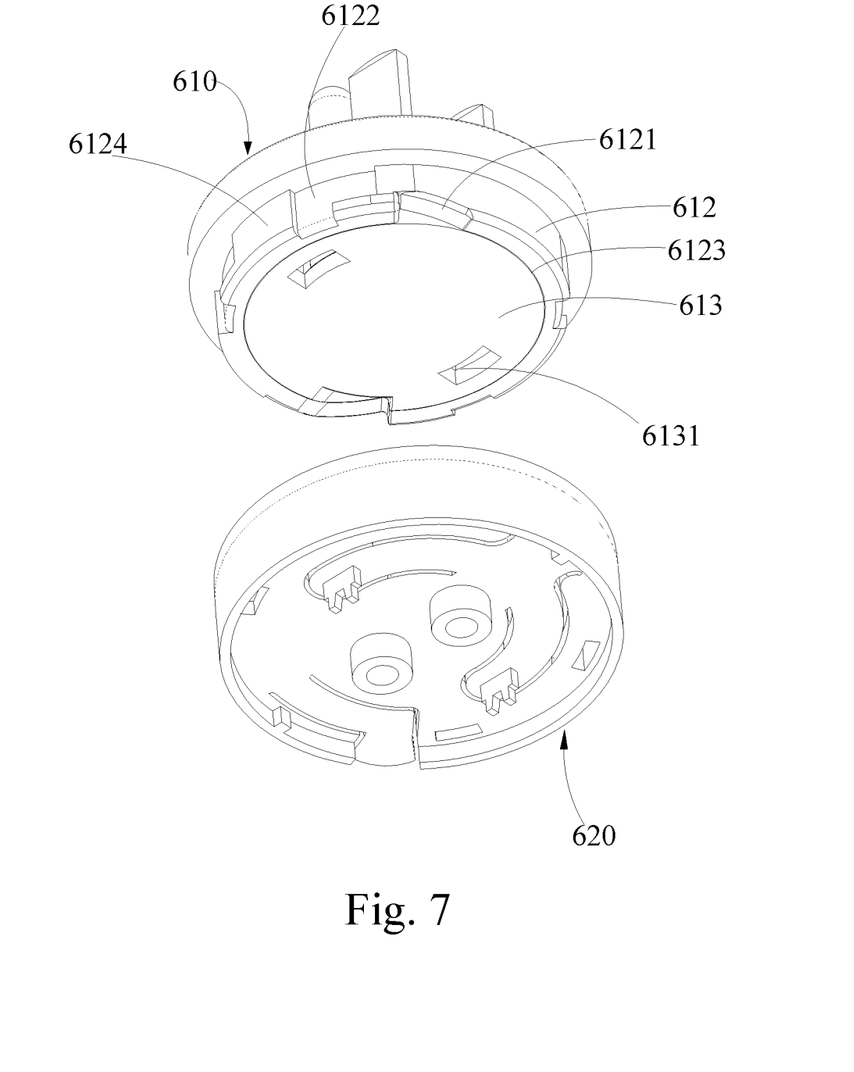
FIG. 7 shows another explosive view of the replaceable plug according to the present invention.

Referring to FIG. 5 to FIG. 7, in another embodiment of the invention, the replaceable plug 600 includes a plug piece 610 and a plug base 620, the plug base 620 is fixedly connected with a side surface of the bottom shell 100. A first bottom surface 614 of the plug piece 610 is provided with an inserting portion 612 and conductive sheets 611, the inserting portion 612 is second hollow cylinder with a port 6123, the conductive sheets 611 are contained in the inserting portion 612, the port 6123 is provided with a cover plate 613, the cover plate 613 is provided with a number of avoidance holes 6131. The plug base 620 is provided with an inserting groove 621, the plug piece 610 is inserted into the inserting groove 621 and is rotatably connected to the plug base 620, the plug base 620 is provided with electrical connecting columns 622, the electrical connecting columns 622 pass through the avoidance holes 6131 and contact with the conductive sheets 611, the inserting groove 621 is provided with a second bottom wall 6211 and a sidewall 6212, the second bottom wall 6211 is provided with an elastic bump 62111, the elastic bump 62111 is in a slope shape and is connected with an unlock button 62112, the sidewall 6212 is provided with a number of position limiting protrusions 62121. The port 6123 of the inserting portion 612 is provided with a slope shaped groove 6121, an outer side surface 6124 of the inserting portion 612 is provided with L-shaped grooves 6122. The elastic bump 62111 can rotate unidirectionally and be stuck in the slope shaped groove 6121, the position limiting protrusions 62121 can slide into the L-shaped grooves 6122 and slide along a circumference of the inserting portion 612 in the L-shaped grooves 6122.

When the plug base 620 and the plug piece 610 are locking, the plug piece 610 is inserted into the inserting groove 621, the position limiting protrusion 62121 can slide into the L-shaped groove, the plug piece 610 can be rotated clockwise, the elastic bump 62111 is stuck in the slope shaped groove 6121, and then the plug base 620 and the plug piece 610 are locked. When the plug base 620 and the plug piece 610 are unlocking, the unlock button 62112 is pressed, the elastic bump 62111 is pressed down and exited from the slope shaped groove 6121, the plug piece 610 is rotated anticlockwise until the position limiting protrusion 62121 is rotated to the outlet of the L-shaped groove, and the plug piece 610 is pulled out. In this embodiment, the clockwise direction is the locking direction, and the counter clockwise direction is the unlocking direction. In another embodiment of the utility model, the locking direction can also be anticlockwise, and the unlocking direction can also be clockwise.

Referring to FIG. 3, in another embodiment of the invention, the bottom outer surface 360 of the transparent supporting base 300 is provided with a first sealing ring 340. The first sealing ring 340 improves the sealing performance.

Referring to FIG. 3, in another embodiment of the invention, a second inner surface 520 of the transparent encloser 500 is provided with a transparent inner sleeve 800. The transparent inner sleeve 800 can be made of transparent plastic material, glass material or crystal material, more preferably acrylic material.

Referring to FIG. 3, in another embodiment of the invention, a second sealing ring 820 is arranged between a bottom 830 of the transparent inner sleeve 800 and the bottom shell 100. The second sealing ring 820 improves the sealing performance.

Figure 8:
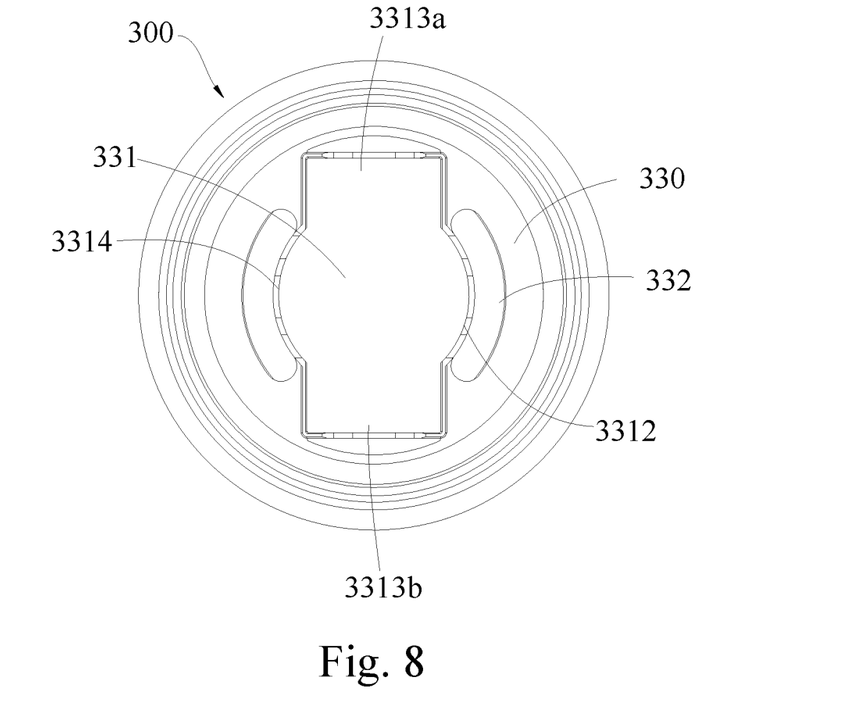
FIG. 8 shows a top view of the transparent supporting base according to the present invention.

Referring to FIG. 8, in another embodiment of the invention, two ends 3313a,3313b of the groove 331 for the essential oil piece 3311 are square, and both sides of a middle part of the groove 331 have arc parts 3312 which protrude outwards. The groove 331 can be used to place both square and circular essential oil pieces.

Referring to FIG. 8, in another embodiment of the invention, the perforated board 330 is provided with hollowed-out hole for ventilation 332, the hollowed-out hole for ventilation 332 is located outside a circumference 3314 of the groove 331. Specifically, the number of the hollowed-out hole 332 for ventilation 332 is preferably four, and the four hollowed-out holes 332 for ventilation are arranged on the outside of the periphery of the groove for essential oil piece 331.

Referring to FIG. 3, in another embodiment of the invention, the light source 400 is LED lamp, the light source 400 is fixed on a second bottom surface 333 of the perforated board 330.

Figure 1:
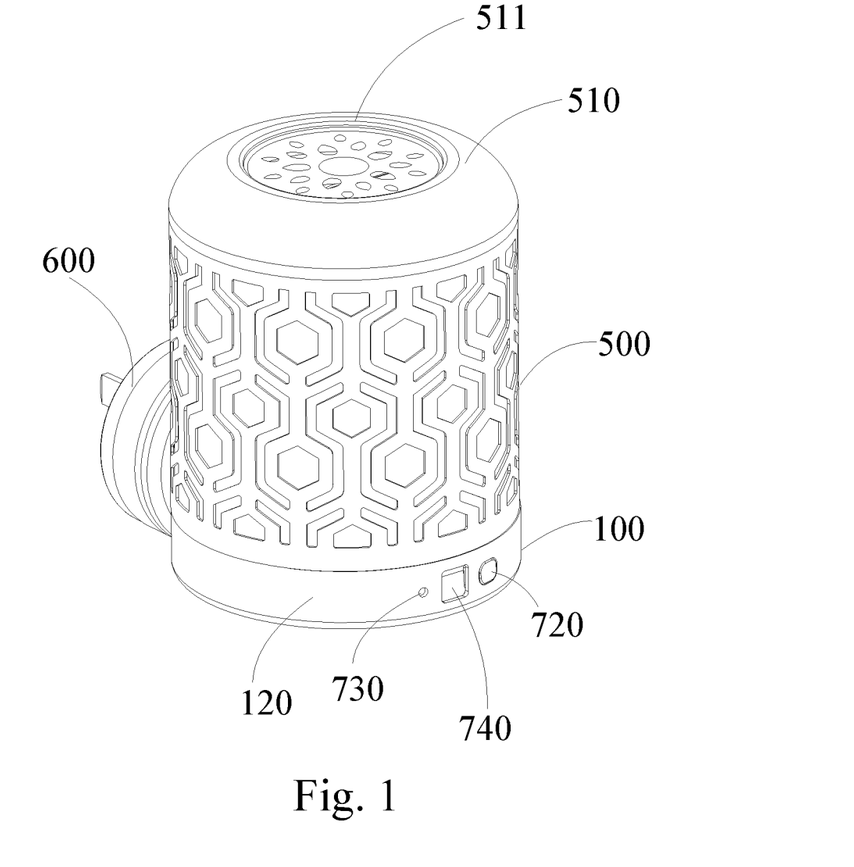
FIG. 1 shows a perspective view of the small night lamp with spreading fragrance function according to the present invention.

Referring to FIG. 1, in another embodiment of the invention, the switch controller includes a PCBA board 710, an light sensor 730, a human body sensor 740 and a switch key 720. The PCBA board 710 is arranged in the accommodating groove 110. The switch key 720, the light sensor 730 and the human body sensor 740 are arranged on an outer surface 120 of the bottom shell 100 and are connected with the PCBA board 710. The switch of the fan 200 and the light source 400 can be controlled by the switch key 720. The light sensor 730 can sense the light intensity. When the light is dark, the light sensor 730 will feedback the induction signal to the PCBA board 710, and the PCBA board 710 turns on the light source 400. The human body sensor 740 can sense and recognize the human body. When the user closes the night light with spreading fragrance function, the human body sensor 740 recognizes the human body and feeds back the signal to the PCBA board 710, which turns on the light source 400 and turns off the light source 400 when the user is far away from the small night lamp with spreading fragrance function.

The above is only better embodiments in the invention and is not used to limit the invention. Any modification, equivalent replacement and improvement made within the spirit and principles of the invention shall be included in the protection of the invention.

The invention claimed is:

1. Small night lamp with spreading fragrance function, wherein including:
   a bottom shell, said bottom shell is provided with an accommodating groove with a first bottom wall, a side surface and a groove opening; said first bottom wall is provided with a number of air inlet holes and an electrical connector; said accommodating groove is provided with a switch controller; said switch controller is electrically connected with said electrical connector;
   a fan, said fan is arranged above said accommodating groove;
   a transparent supporting base, said transparent supporting base is a first hollow cylinder with a lower opening and an upper opening, said lower opening is closely matched with said groove opening; a first inner surface of said transparent supporting base is provided with a perforated board, a top surface of said perforated board is provided with a groove for containing an essential oil piece, said essential oil piece is placed in said groove;
   a light source, said light source is arranged in said transparent supporting base; and,
   a transparent encloser, said transparent encloser is movably covered an outer side of said transparent supporting base, and a bottom edge of said first hollow cylinder is tightly matched with said bottom shell; light emitted by said light source penetrates through said transparent encloser; a top cover is arranged on said transparent encloser, said top cover is correspondingly above said perforated board and is provided with a number of air outlet holes; said upper opening is closely touched to said top cover.

2. The small night lamp with spreading fragrance function according to claim 1, wherein said electrical connector is a fixed plug or a replaceable plug.

3. The small night lamp with spreading fragrance function according to claim 2, wherein said replaceable plug includes a plug piece and a plug base, said plug base is fixedly connected with said side surface of said bottom shell; a first bottom surface of said plug piece is provided with an inserting portion and conductive sheets, said inserting portion is second hollow cylinder with a port, said conductive sheets are contained in said inserting portion, said port is provided with a cover plate, said cover plate is provided with a number of avoidance holes; said plug base is provided with an inserting groove, said plug piece is inserted into said inserting groove and is rotatably connected to said plug base; said plug base is provided with electrical connecting columns, said electrical connecting columns pass through said avoidance holes and contact with said conductive sheets, said inserting groove is provided with a second bottom wall and a sidewall, said second bottom wall is provided with an elastic bump, said elastic bump is in a slope shape and is connected with an unlock button, said sidewall is provided with a number of position limiting protrusions; said port of said inserting portion is provided with a slope shaped groove, an outer side surface of the inserting portion is provided with L-shaped grooves; said elastic bump can rotate unidirectionally and be stuck in said slope shaped groove, said position limiting protrusions can slide into said L-shaped grooves and slide along a circumference of said inserting portion in said L-shaped grooves.

4. The small night lamp with spreading fragrance function according to claim 1, wherein a bottom outer surface of said transparent supporting base is provided with a first sealing ring.

5. The small night lamp with spreading fragrance function according to claim 1, wherein a second inner surface of said transparent encloser is provided with a transparent inner sleeve.

6. The small night lamp with spreading fragrance function according to claim 5, wherein a second sealing ring is arranged between a bottom of said transparent inner sleeve and said bottom shell.

7. The small night lamp with spreading fragrance function according to claim 1, wherein two ends of said groove for essential oil piece are square, and both sides of a middle of said groove have arc parts which protrude outwards.

8. The small night lamp with spreading fragrance function according to claim 1, wherein said perforated board is provided with hollowed-out hole for ventilation, said hollowed-out hole for ventilation is located outside a circumference of said groove.

9. The small night lamp with spreading fragrance function according to claim 2, wherein said perforated board is provided with hollowed-out hole for ventilation, said hollowed-out hole for ventilation is located outside a circumference of said groove.

10. The small night lamp with spreading fragrance function according to claim 3, wherein said perforated board is provided with hollowed-out hole for ventilation, said hollowed-out hole for ventilation is located outside a circumference of said groove.

11. The small night lamp with spreading fragrance function according to claim 1, wherein said light source is LED lamp, said light source is fixed on a second bottom surface of said perforated board.

12. The small night lamp with spreading fragrance function according to claim 2, wherein said light source is LED lamp, said light source is fixed on a bottom surface of said perforated board.

13. The small night lamp with spreading fragrance function according to claim 3, wherein said light source is LED lamp, said light source is fixed on a bottom surface of said perforated board.

14. The small night lamp with spreading fragrance function according to claim 1, wherein said switch controller includes a PCBA board, an light sensor, a human body sensor and a switch key, said PCBA board is arranged in said accommodating groove; said switch key, said light sensor and said human body sensor is arranged on an outer surface of said bottom shell and are connected with said PCBA board.

15. The small night lamp with spreading fragrance function according to claim 2, wherein said switch controller includes a PCBA board, an light sensor, a human body sensor and a switch key; said PCBA board is arranged in said accommodating groove; said switch key, said light sensor and said human body sensor are arranged on an outer surface of said bottom shell and are connected with said PCBA board.

16. The small night lamp with spreading fragrance function according to claim 3, wherein said switch controller includes a PCBA board, an light sensor, a human body sensor and a switch key; said PCBA board is arranged in said accommodating groove; said switch key, said light sensor and said human body sensor are arranged on an outer surface of said bottom shell and are connected with said PCBA board.

17. The small night lamp with spreading fragrance function according to claim 4, wherein said switch controller includes a PCBA board, an light sensor, a human body sensor and a switch key; said PCBA board is arranged in said accommodating groove; said switch key, said light sensor and said human body sensor are arranged on an outer surface of said bottom shell and are connected with said PCBA board.

18. The small night lamp with spreading fragrance function according to claim 5, wherein said switch controller includes a PCBA board, an light sensor, a human body sensor and a switch key; said PCBA board is arranged in said accommodating groove; said switch key, said light sensor and said human body sensor are arranged on an outer surface of said bottom shell and are connected with said PCBA board.

19. The small night lamp with spreading fragrance function according to claim 6, wherein said switch controller includes a PCBA board, an light sensor, a human body sensor and a switch key; said PCBA board is arranged in said accommodating groove; said switch key, said light sensor and said human body sensor are arranged on an outer surface of said bottom shell and are connected with said PCBA board.

20. The small night lamp with spreading fragrance function according to claim 7, wherein said switch controller includes a PCBA board, an light sensor, a human body sensor and a switch key; said PCBA board is arranged in said accommodating groove; said switch key, said light sensor and said human body sensor are arranged on an outer surface of said bottom shell and are connected with said PCBA board.

* * * * *